(12) United States Patent
Nagao (10) Patent No.: US 9,486,166 B2
(45) Date of Patent: Nov. 8, 2016

(54) PUNCTURING NEEDLE CARTRIDGE AND PUNCTURING INSTRUMENT

(71) Applicant: Panasonic Healthcare Holdings Co., Ltd., Tokyo (JP)

(72) Inventor: Akio Nagao, Kagawa (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 200 days.

(21) Appl. No.: 14/401,983

(22) PCT Filed: Apr. 5, 2013

(86) PCT No.: PCT/JP2013/002367
§ 371 (c)(1),
(2) Date: Nov. 18, 2014

(87) PCT Pub. No.: WO2013/171963
PCT Pub. Date: Nov. 21, 2013

(65) Prior Publication Data
US 2015/0142037 A1    May 21, 2015

(30) Foreign Application Priority Data

May 18, 2012  (JP) ................................. 2012-114375

(51) Int. Cl.
*A61B 17/14* (2006.01)
*A61B 5/151* (2006.01)
*A61B 5/15* (2006.01)

(52) U.S. Cl.
CPC ......... *A61B 5/15194* (2013.01); *A61B 5/1411* (2013.01); *A61B 5/150549* (2013.01); (Continued)

(58) Field of Classification Search
CPC ................. A61B 5/150534; A61B 5/150541; A61B 5/150549; A61B 5/150572; A61B 5/150557; A61B 5/150564; A61B 5/15192; A61B 5/15194; A61B 5/15196; A61B 5/150053; A61B 5/150083; A61B 5/151126; A61B 5/15128; A61B 5/150175; A61B 5/15019; A61B 5/150183; A61B 5/150198; A61B 5/150946; A61B 5/150885; A61B 5/150916
See application file for complete search history.

(56) References Cited

U.S. PATENT DOCUMENTS 5,085,640 A * 2/1992 Gibbs .................... A61B 5/154
                                                144/145.1
5,554,166 A    9/1996 Lange et al.
(Continued)

FOREIGN PATENT DOCUMENTS

JP        7-16218      1/1995
JP      2009-77871     4/2009
(Continued)

OTHER PUBLICATIONS

International Search Report issued May 7, 2013 in International (PCT) Application No. PCT/JP2013/002367.

*Primary Examiner* — Jonathan Miles
*Assistant Examiner* — Wade Miles
(74) *Attorney, Agent, or Firm* — Wenderoth, Lind & Ponack, L.L.P.

(57) ABSTRACT

A puncture needle cartridge (2) comprises: a columnar lancet body (6) having a puncture needle on the front end side and a puncture instrument mount (5) on the rear end side; a protective cap (13) covering the puncture needle and having a shape extending toward the front end; a skin contact part (10) placed in front of the tip of the puncture needle, having a planar shape perpendicular to the puncture needle, and formed with a through hole to put the protective cap (13) through; an elongate plate-like extension (9) extending from the skin contact part (10) toward the rear end; and an elastic object (8) for coupling the extension (9) to the lancet body (6) and making the tip of the puncture needle be biased to be located in the rear end side behind the skin contact part (10).

6 Claims, 13 Drawing Sheets

(52) U.S. Cl.
CPC .... *A61B5/150641* (2013.01); *A61B 5/150022* (2013.01); *A61B 5/15113* (2013.01); *A61B 5/15117* (2013.01); *A61B 5/15186* (2013.01); *A61B 5/150389* (2013.01); *A61B 5/150503* (2013.01)

(56) References Cited

U.S. PATENT DOCUMENTS

| | | | | |
|---|---|---|---|---|
| 5,707,384 | A * | 1/1998 | Kim | A61B 5/1411 606/181 |
| 6,322,574 | B1 * | 11/2001 | Lloyd | A61B 5/150717 606/181 |
| 2002/0120216 | A1 * | 8/2002 | Fritz | A61B 5/1411 600/583 |
| 2004/0249406 | A1 * | 12/2004 | Griffin | A61B 5/1411 606/182 |
| 2005/0015019 | A1 * | 1/2005 | Honda | A61B 5/1411 600/576 |
| 2005/0085839 | A1 * | 4/2005 | Allen | A61B 5/1411 606/181 |
| 2005/0277849 | A1 * | 12/2005 | Wong | A61B 5/1411 600/583 |
| 2007/0135828 | A1 * | 6/2007 | Rutynowski | A61B 5/1411 606/181 |
| 2007/0185515 | A1 * | 8/2007 | Stout | A61B 5/1411 606/181 |
| 2007/0293882 | A1 * | 12/2007 | Harttig | A61B 5/1411 606/181 |
| 2009/0156963 | A1 * | 6/2009 | Noble | A61B 5/1405 600/582 |
| 2009/0264911 | A1 * | 10/2009 | Kim | A61B 5/1411 606/182 |
| 2010/0318111 | A1 * | 12/2010 | Sarna | A61B 5/1411 606/182 |
| 2011/0196409 | A1 | 8/2011 | Nagao et al. | |
| 2012/0095488 | A1 | 4/2012 | Saeki et al. | |
| 2012/0116436 | A1 * | 5/2012 | Wiegel | A61B 5/1411 606/181 |
| 2013/0331879 | A1 | 12/2013 | Nagao et al. | |

FOREIGN PATENT DOCUMENTS

| | | |
|---|---|---|
| JP | 2010-110625 | 5/2010 |
| JP | 2012-85686 | 5/2012 |

* cited by examiner

PUNCTURING NEEDLE CARTRIDGE AND PUNCTURING INSTRUMENT

RELATED APPLICATION

This application claims the benefit of Japanese Patent Application No. 2012-114375 filed on May 18, 2012 in Japan, the contents of which are incorporated herein by reference.

TECHNICAL FIELD

The invention relates to a puncture needle cartridge for puncturing skin to allow the blood to be oozed in order to, for example, measure the blood sugar level, and to a puncture instrument using the cartridge.

BACKGROUND ART

The configuration of such a puncture needle cartridge and a puncture instrument using it would conventionally be as follows. That is, a puncture needle cartridge would comprise: a columnar lancet body having a puncture needle on the front end side and a puncture instrument mount on the rear end side; and a protective cap covering the tip of the puncture needle and being provided with an operation part on the front end side. The rear end side of the protective cap would be configured to be coupled to the lancet body via a separating part (e.g. Patent Document 1).

PRIOR ART DOCUMENT

Patent Document

Patent Document 1: Japanese Patent Laid-Open Application No. Hei 7-16218

SUMMARY OF THE INVENTION

Problems to be Solved by the Invention

The above-described conventional example can prevent a puncture needle from accidentally hurting, for example, hands when the puncture needle cartridge is mounted on a puncture instrument since the tip of the puncture needle is covered by the protective cap.

In addition, the operability is extremely good because, when puncture is performed with the puncture needle, it can be exposed just by twisting the operation part to break the separating part for the removal of the protective cap.

The exposed puncture needle, however, can sometimes hurt hands when the puncture needle cartridge is disposed of after puncture, and there is a requirement, for higher safety.

A purpose of the invention is thus to increase safety.

Means for Solving the Problems

In order to achieve this purpose, the invention comprises: a columnar lancet body having a puncture needle on the front end side and a puncture instrument mount on the rear end side; a protective cap covering the puncture needle and having a shape extending toward the front end; a skin contact part placed in front of the tip of the puncture needle, having a planar shape perpendicular to the puncture needle, and formed with a through hole to put the protective cap through; an elongate plate-like extension extending from the skin contact part toward the rear end; and an elastic object for coupling the extension to the lancet body and making the tip of the puncture needle be biased to be located in the rear end side behind the skin contact part. This allows the intended objective to be achieved.

Advantages of the Invention

In the present invention, the skin contact part having a planar shape perpendicular to the puncture needle exists in front of the puncture needle even when the protective cap is separated from the lancet body, and therefore safety is increased since the puncture needle will not accidentally hurt hands or the like when the puncture needle cartridge is removed from the puncture instrument for disposal.

EMBODIMENTS OF THE INVENTION

Embodiments of the invention will be described below with reference to the accompanying drawings.

Embodiment 1

Figure 1:
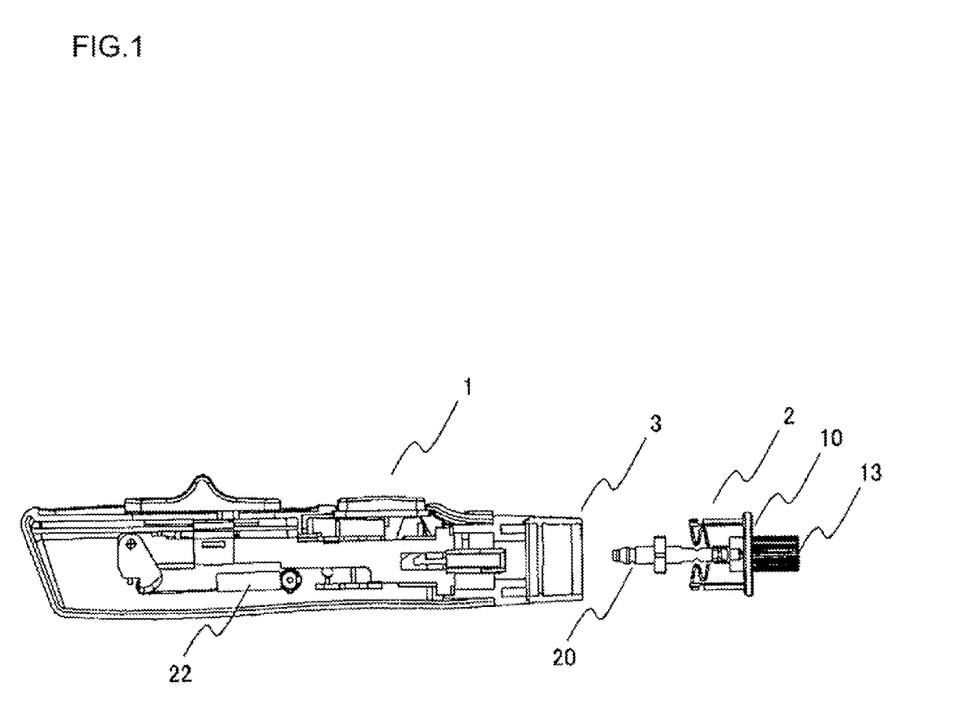
FIG. 1 shows a state where a puncture needle cartridge according to an embodiment of the invention is not yet mounted on a puncture instrument.
Figure 2:
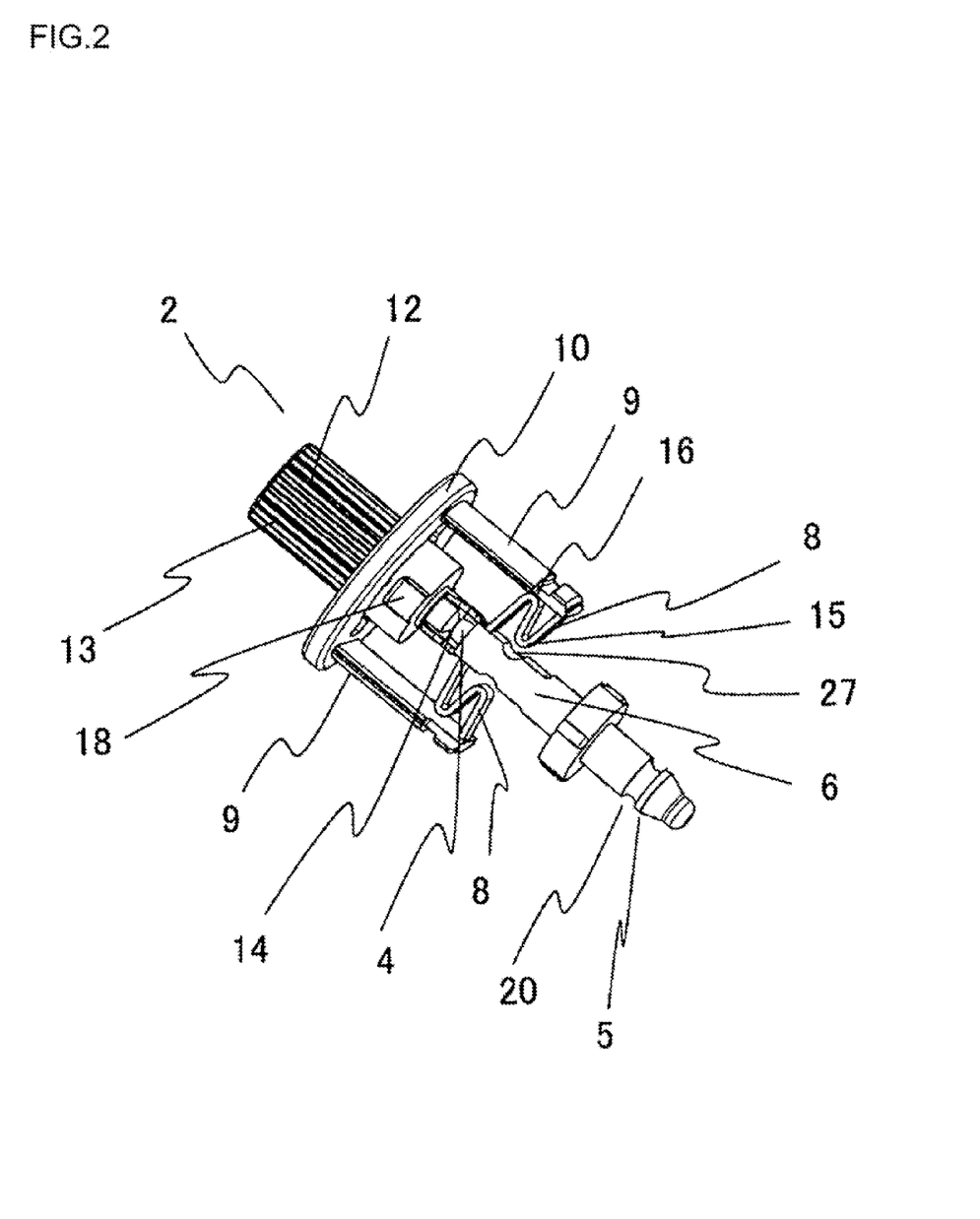
FIG. 2 is a perspective view of the puncture needle cartridge according to the embodiment of the invention.
Figure 3:
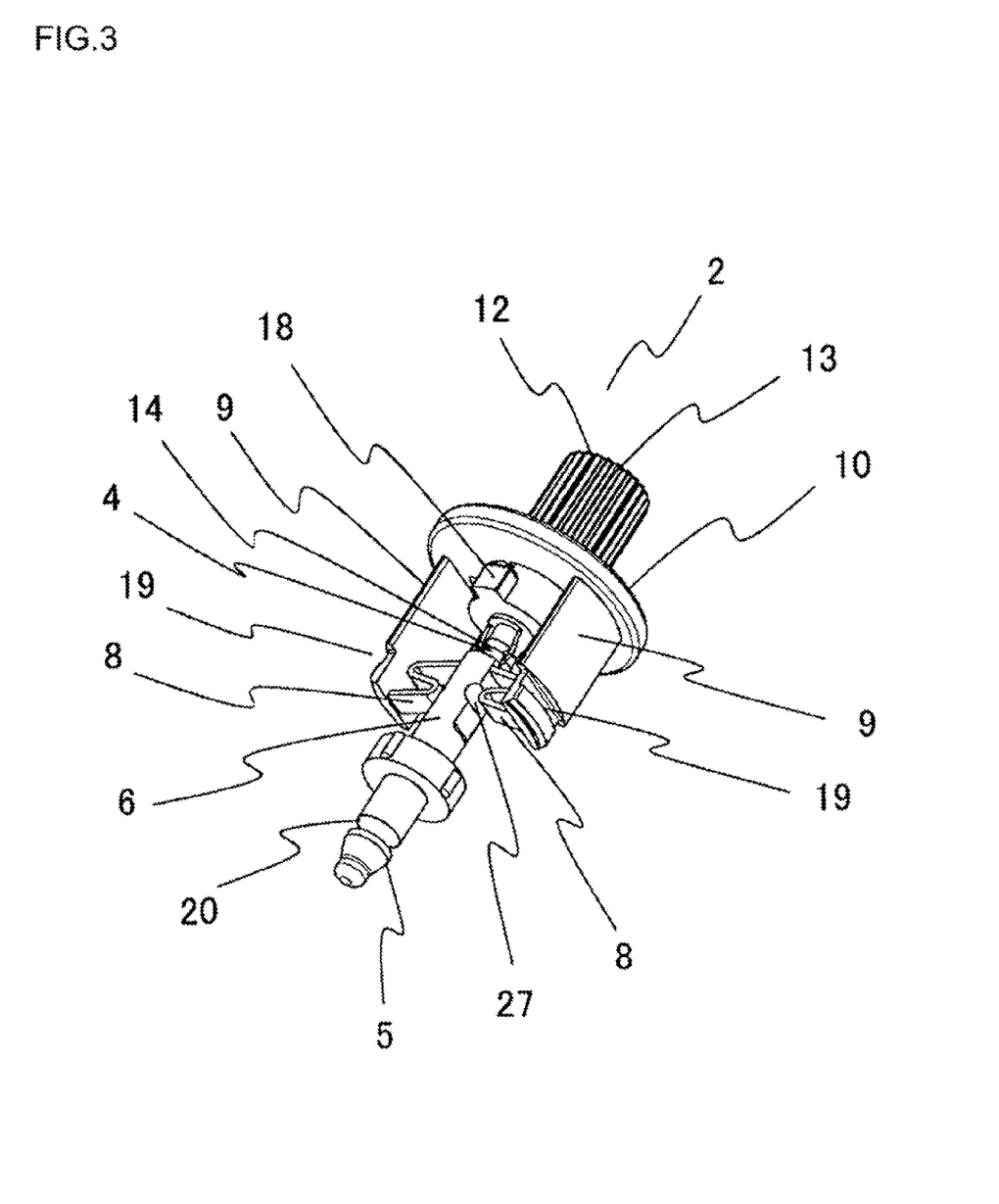
FIG. 3 is a perspective view of the puncture needle cartridge according to the embodiment of the invention.
Figure 4:
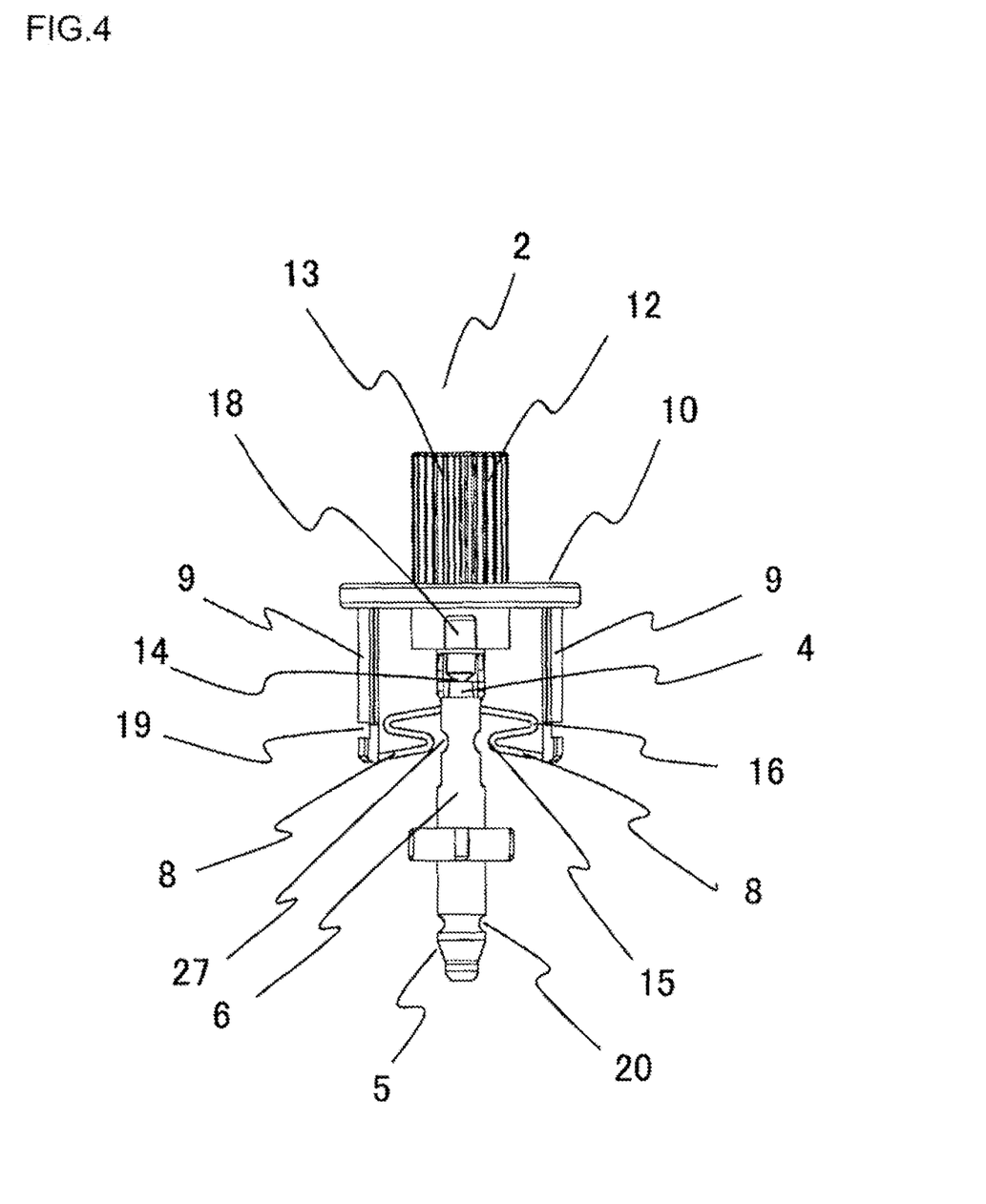
FIG. 4 is a front view of the puncture needle cartridge according to the embodiment of the invention.
Figure 5:
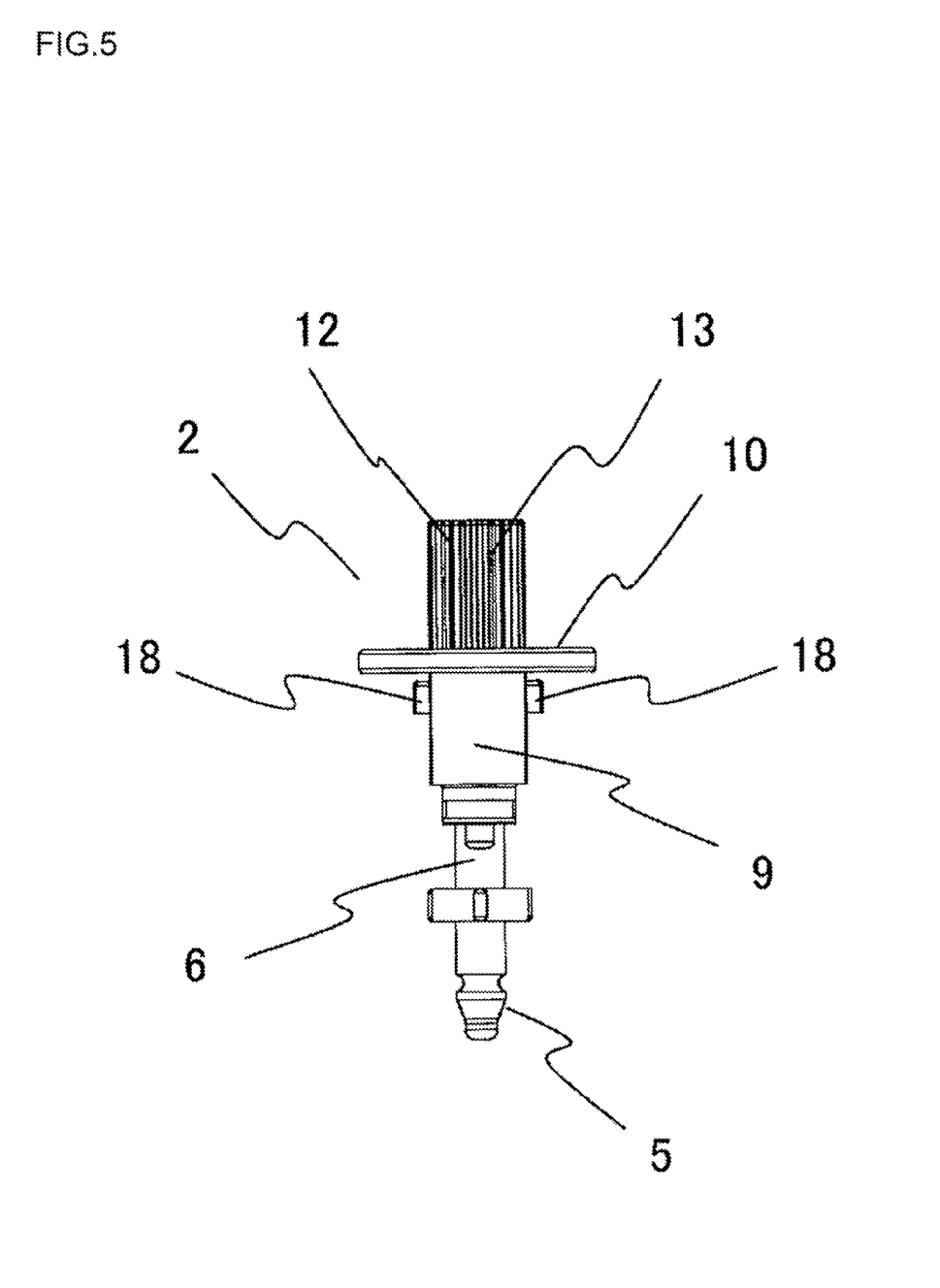
FIG. 5 is a side view of the puncture needle cartridge according to the embodiment of the invention.

FIG. 1 shows a puncture instrument indicated with 1, on the front end side of which is provided a holder 3 into which a puncture needle cartridge 2 is inserted.

The puncture needle cartridge 2 has a lancet body 6, a skin contact part 10, and a protective cap 13 as shown in FIGS. 2 to 6. The lancet body 6 has a cylindrical shape. The lancet body 6 has a puncture needle holder 4 for holding a puncture needle 7 (see FIGS. 8, 10, etc.) on the front end side, and has a puncture instrument mount 6 on the rear end side.

The rear end side of the protective cap 13 is coupled to the puncture needle holder 4 of the lancet body 6 via a separating part 14. The protective cap 13 covers the tip of the puncture needle 7. The protective cap 13 is provided with a cylindrical operation part 12 on the front end side. Behind the operation part 12 is provided guide protrusions 18 for rotating the operation part 12.

Figure 6:
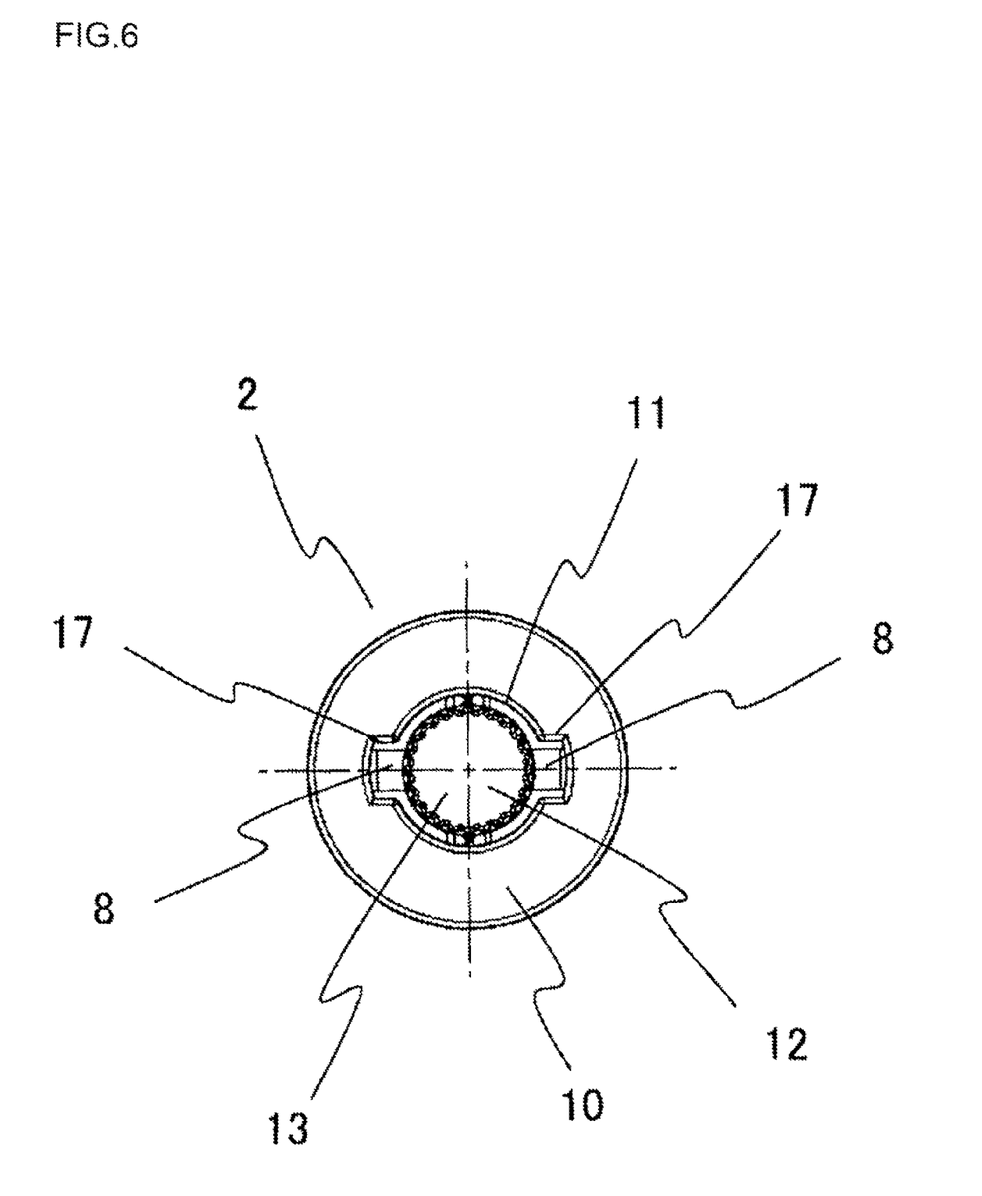
FIG. 6 is a top view of the puncture needle cartridge according to the embodiment of the invention.

The skin contact part 10, in front of the puncture needle 7, has a disk shape perpendicular to the puncture needle 7 (see FIG. 6 etc.). While the example where the skin contact part 10 has a disk shape is given in this embodiment, the shape is not limited to disk, but may also be rectangle or the like. A circular through hole 11 to put the protective cap 13 through is formed on the skin contact part 10. In the through hole 11 are formed cuts 17 which are cut outward from the through hole 11. Two cuts 17 are formed in positions opposite to each other across the center of the through hole 11. As can be seen from FIGS. 6 and 9, the cuts 17 are made in order for the guide protrusions 18 to pass when the protective cap 13 is removed.

Extensions 9 extending toward the rear end are provided on the outer regions of the skin contact part 10. The extensions 9 are opposed to each other across the through hole 11, being approximately parallel to the lancet body 6. Each extension 9 is an elongate plate-like member, the rear end side of which is deformable toward the lancet body 6. Elastic objects 8 couple the extensions 9 to the lancet body 6. Each elastic object 8 is integrally connected on one end to the front end portion of the lancet body 6, and is integrally connected on the other end to the rear end portion of each extension 9, Each elastic object 8 is shaped like an elongate plate-like member being folded. As described below with reference to FIGS. 10, 11, etc., the elastic objects make the tip of the puncture needle be biased to be located in the rear end side behind the skin contact part 10.

Each elastic object 8 has, between lancet body 6 and each extension 9, a first bent portion 15 which bends convexly toward the lancet body 6 and a second bent portion 16 which bends convexly toward each extension 9. There is space between the first bent portion 15 and the lancet body 6 and between the second bent portion 16 and each extension 9. This allows the rear portion of each extension 9 to be deformable toward the lancet body 6.

While the example where there are two extensions 9 and two elastic objects 8 for coupling the extensions 9 is given in this embodiment, the number of the extensions 9 and elastic objects 8 is not limited to two, but may also be three, four, or more. When three or more extensions 9 and elastic objects 8 are to be provided, however, it is desirable to arrange them at regular intervals around the lancet body 6. This allows the lancet body 6 to move straight in a direction perpendicular to the skin contact part 10 for an appropriate puncture.

Figure 9:
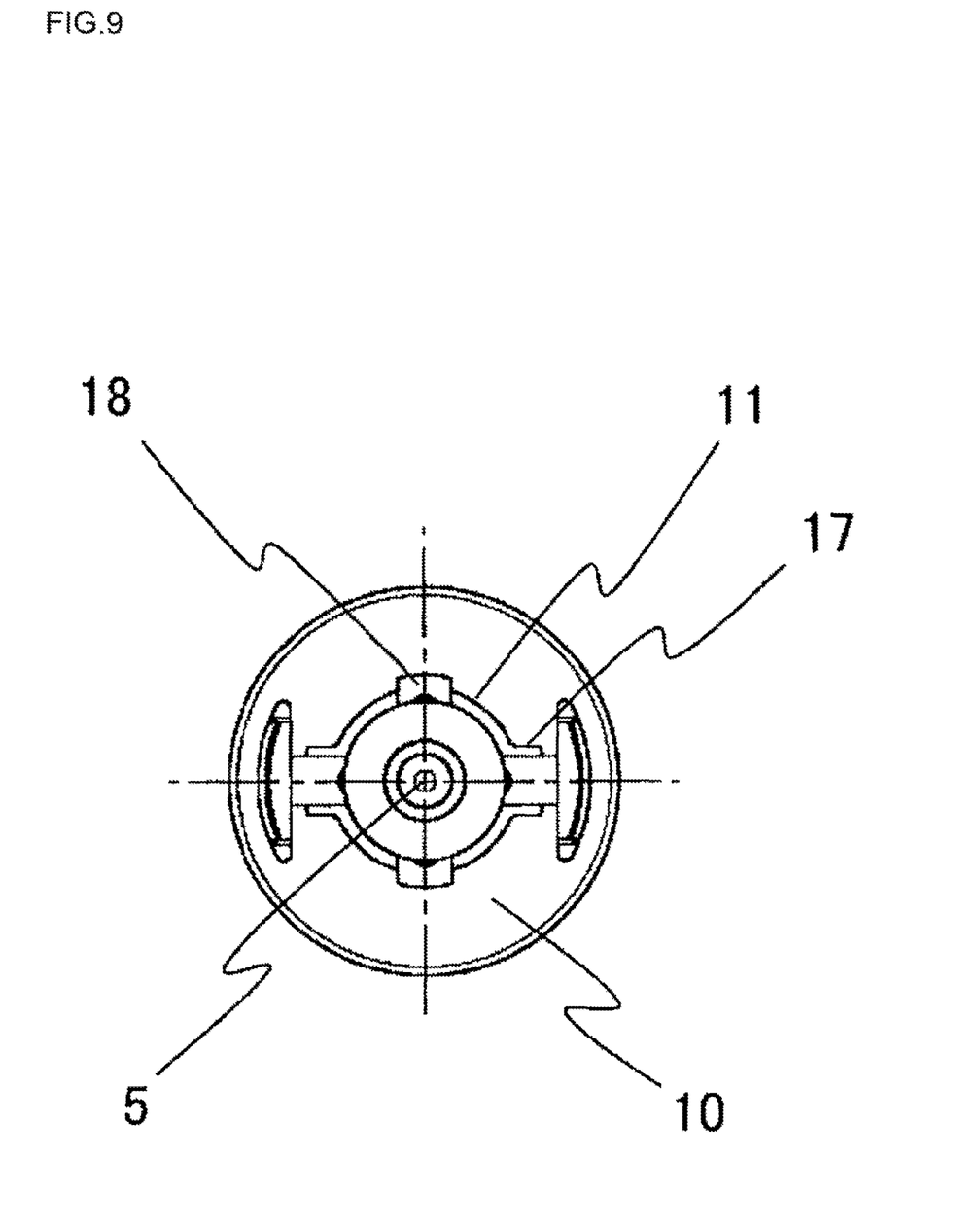
FIG. 9 is a back view showing a state where the puncture needle cartridge according to the embodiment of the invention is mounted on the puncture instrument.

FIG. 6 is a view of the puncture needle cartridge 2 seen from the operation part 12 of the protective cap 13, and FIG. 9 is a view of the puncture needle cartridge 2 seen from the puncture instrument mount 5. Rotating the protective cap 13 90 degrees with the operation part 12 makes the separating part 14 be twisted off and makes the guide protrusions 18 and the cuts 17 be coincided with each other, so that the protective cap 13 separated from the lancet body 6 can be pulled out forward.

A hollow 19 is provided on the rear outer surface of each extension 9 (opposite to the surface facing the lancet body 6). The puncture instrument 1 holds the hollows 19 and a hollow 20 of the puncture instrument mount 5.

In the present embodiment, the lancet body 6, the elastic objects 8, the extension the skin contact part 10, and the protective cap 13 are integrally formed of plastic.

The puncture needle 7 in this configuration will not hurt fingers or the like since the tip of the puncture needle 7 is covered by the protective cap 13.

When blood is to be collected from a finger with this configuration in order to, for example, measure the blood sugar level, the puncture needle cartridge 2 is made to be held by the holder 3 of the puncture instrument 1.

Figure 7:
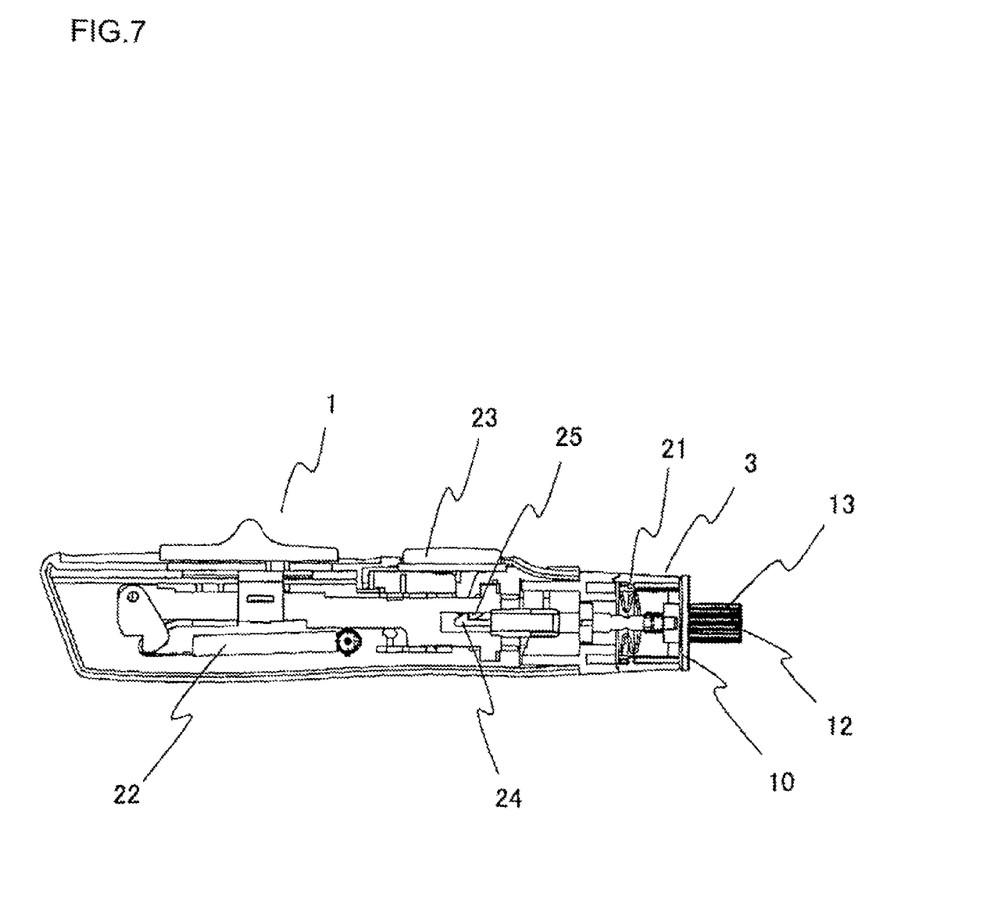
FIG. 7 shows a state where the puncture needle cartridge according to the embodiment of the invention is mounted on the puncture instrument.

Specifically, the rear end side of the puncture needle cartridge 2 is inserted into the holder 3 as shown in FIG. 1, resulting in the state shown in FIG. 7.

This involves protrusions 21, provided on the holder 3, fitting in the hollows 19 of the extensions 9 of the puncture needle cartridge 2, and a protrusion (not shown in the figures) fitting in the hollow 20 of the puncture instrument mount 5. This puts the puncture needle cartridge 2 into a state where it is held by the holder 3 of the puncture instrument 1.

Thus inserting the puncture needle cartridge 2 into the holder 3 stretches a biasing object 22, as shown in FIG. 7, from the state shown in FIG. 1. This allows the biasing object 22 to accumulate biasing force to push forward the lancet body 6 of the puncture needle cartridge 2.

Rotating the operation part 12 in this state makes the separating part 14 of the protective cap 13 be twisted off. This allows the protective cap 13 to be separated from the puncture needle cartridge 2 as shown in FIG. 8 (see the above description referring to FIGS. 6 and 9).

In order for the lancet body 6 of the puncture needle cartridge 2 not to rotate when the operation part 12 is rotated, the protrusions 21 to hold the extensions 9 are provided on the holder 3 of the puncture instrument 1.

Figure 8:
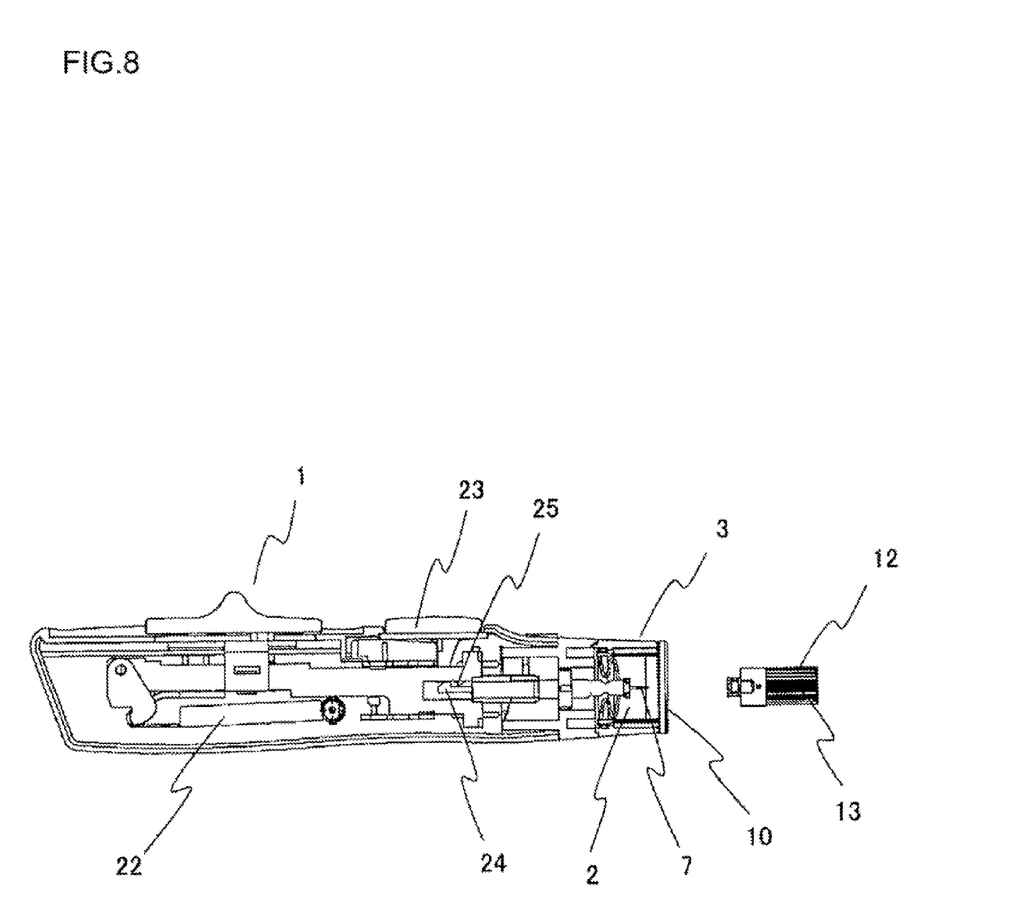
FIG. 8 shows a state where the puncture needle cartridge according to the embodiment of the invention is mounted on the puncture instrument and a protective cap is separated.
Figure 10:
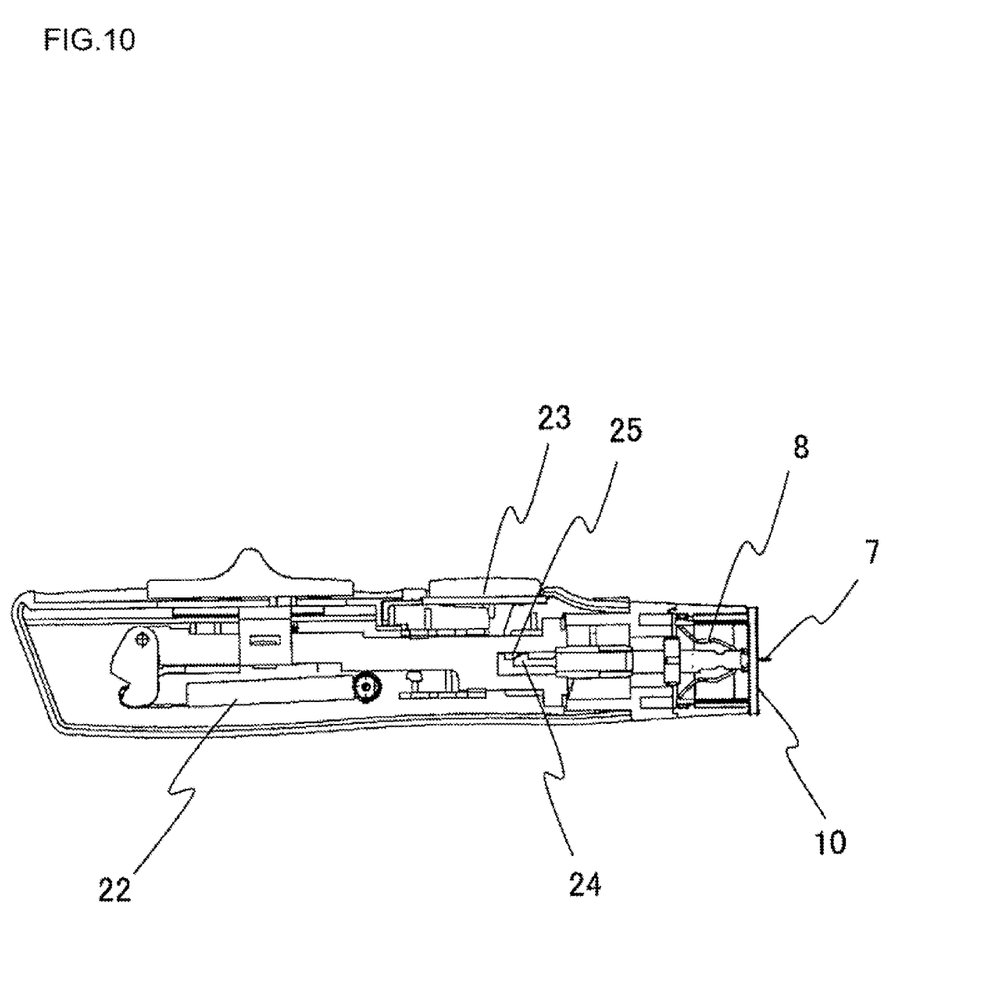
FIG. 10 shows a state where the puncture needle cartridge according to the embodiment of the invention is mounted on the puncture instrument and puncture is being performed.

In this state shown in FIG. 8, bringing the skin contact part 10 into contact with a finger or the like and then operating an operation button 23 makes the puncture needle 7 stick out through the through hole 11 of the skin contact part 10, as shown in FIG. 10, and puncture the finger. Blood is thus collected.

Specifically, in a state where the puncture needle cartridge 2 is mounted on the holder 3 of the puncture instrument 1 as shown in FIG. 7, a lock mechanism 24 is locked by a stopper 25. Pressing in the operation button 23 makes the lock mechanism 24 be pushed down, the lock by the stopper 25 be released, and the lancet body 6 of the puncture needle cartridge 2 be pushed forward by the biasing object 22, as shown in FIG. 10. This makes the puncture needle 7 stick out through the through hole 11 of the skin contact part 10 and puncture the finger, so that blood is collected.

When the puncture needle 7 is pushed forward as above, the elastic objects 8 are stretched as shown in FIG. 10 and therefore do not prevent the puncture needle 7 from being pushed forward.

Figure 11:
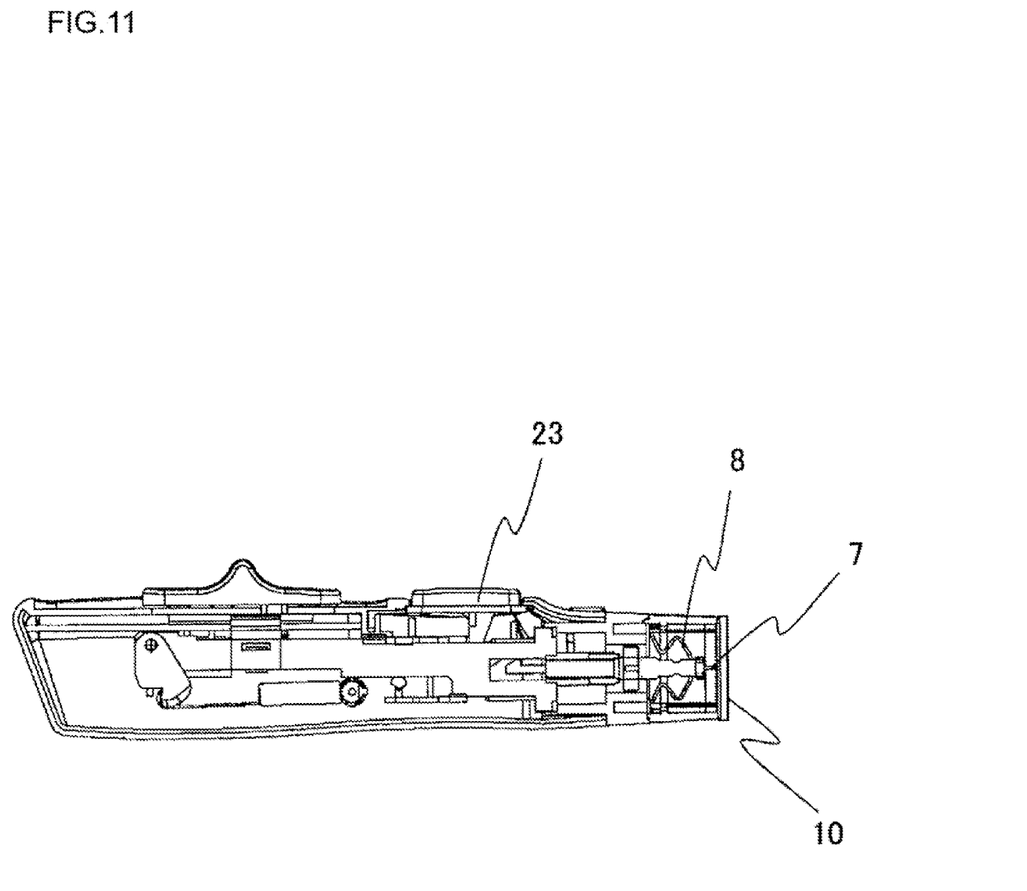
FIG. 11 shows a state where the puncture needle cartridge according to the embodiment of the invention is mounted on the puncture instrument and puncture is already performed.

After the state shown in FIG. 10, the elastic objects 8 contract back to the original state as shown in FIG. 11, so that the puncture needle 7 retracts behind the skin contact part 10, and the blood collection is thus completed.

Being back behind the skin contact part 10 and not exposed then, the puncture needle 7 will not hurt fingers or the like also at this state.

Figure 12:
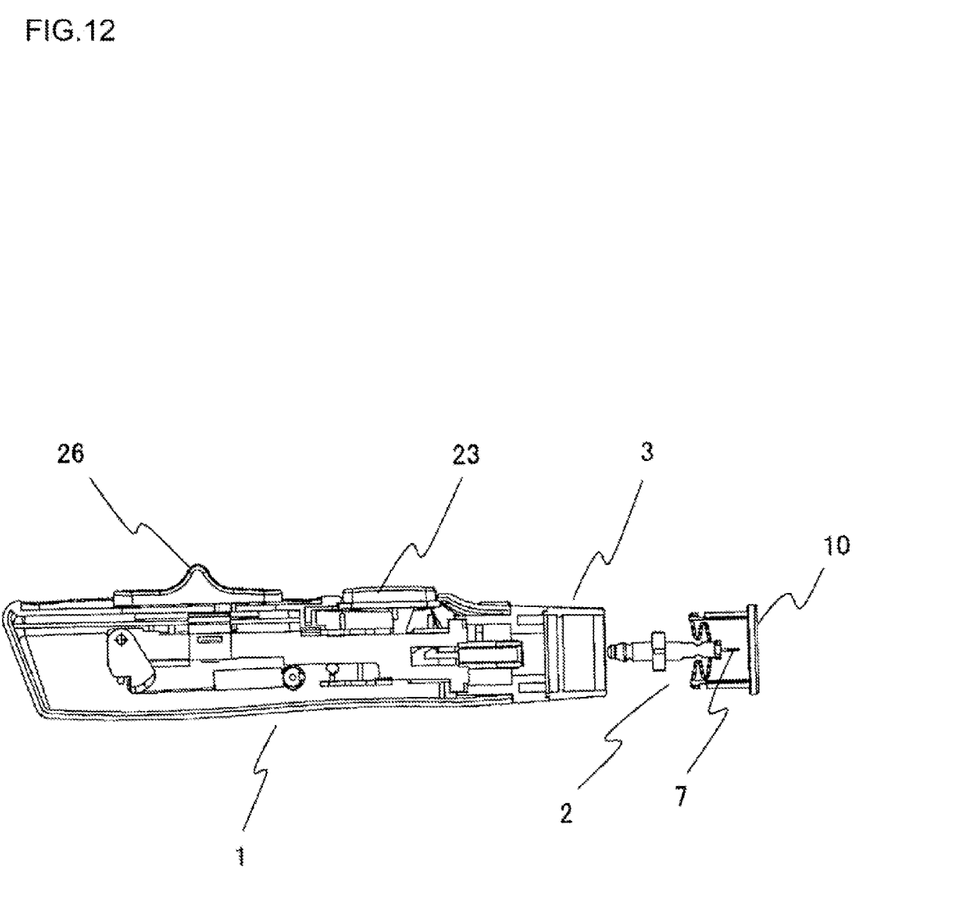
FIG. 12 shows a state where the puncture needle cartridge according to the embodiment of the invention is disposed of from the puncture instrument.

After the completion of such blood collection, the puncture needle cartridge 2 can be removed from the holder 3 of the puncture instrument 1 as shown in FIG. 12.

Specifically, if an ejecting operation lever 26 is moved forward, it pushes forward the lancet body 6 of the puncture needle cartridge 2 via a coupling mechanism (not shown in the figures). This push releases with ease the hollows 19 and hollow 20 held by the holder 3. As a result, the puncture needle cartridge 2 can easily be ejected from the holder 3 of the puncture instrument 1 as shown in FIG. 12.

The skin contact part 10 covers the tip of the puncture needle 7 of the puncture needle cartridge 2 thus ejected from the holder 3 of the puncture instrument 1, as shown in. FIG. 12. Accordingly, fingers will not be hurt when the puncture needle cartridge 2 is, for example, picked up with fingers and thrown into a disposal box (not shown in the figures).

Figure 13:
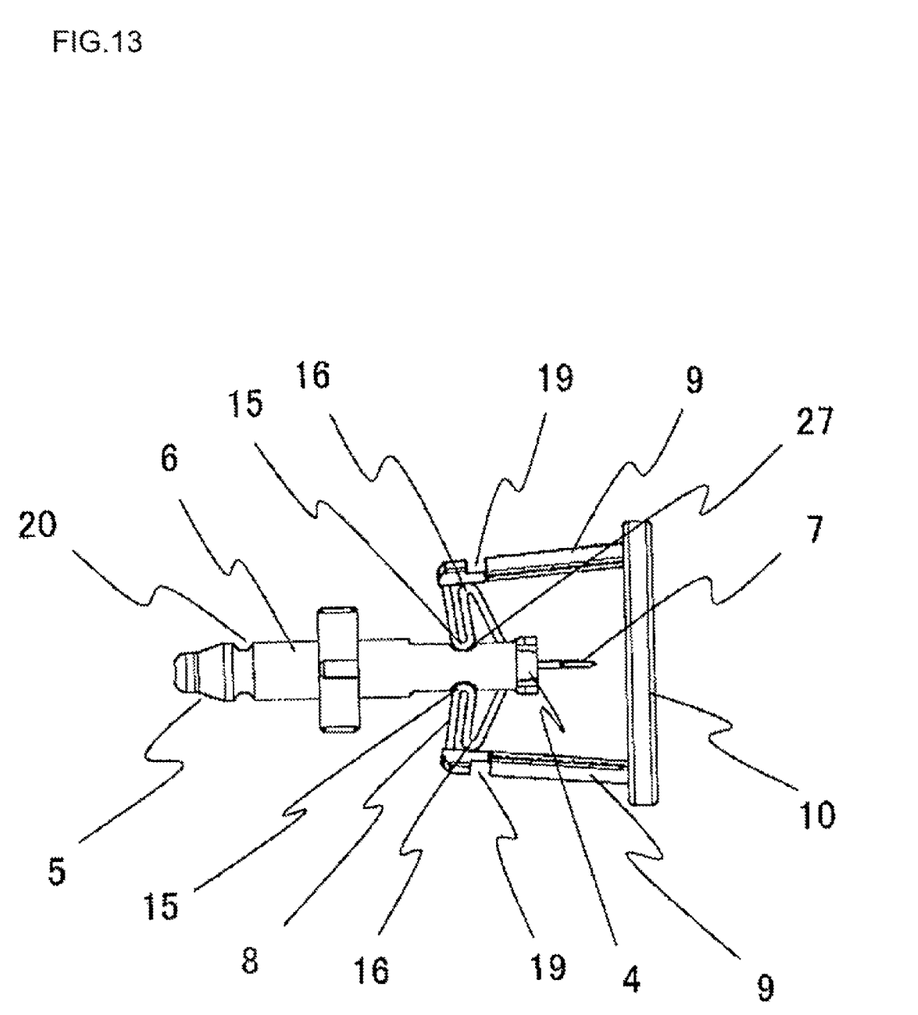
FIG. 13 is a front view showing a state where the puncture needle cartridge according to the embodiment of the invention is disposed of from the puncture instrument.

The region of the extensions 9 might be taken between two fingers when the puncture needle cartridge 2 is, for example, picked up to be thrown into a disposal box. In that case, the rear portions of the extensions 9 would be pushed and bent toward the lancet body 6 as shown in FIG. 13.

Specifically, the rear portions of the extensions 9 are coupled with the elastic objects 8, which are provided with the first and second bent portions 15 and 16 as described above. Accordingly, the rear portions of the extensions 9 being pushed and bent toward the lancet body 6 results in the first bent portions 15 being pressed against the lancet body 6 and in the second bent portions 16 being pressed against the extensions 9.

In this state, the lancet body 6 is substantially fixed to the extensions 9. As a result, the tip of the puncture needle 7 will not stick forward out through the through hole 11 of the skin contact part 10 even though there are the elastic objects 8, and therefore a very high level of safety is achieved.

In addition, the lancet body 6 is provided with hollows 27 in which the first bent portions 15 fit, increasing the above-described effect of preventing the puncture needle 7 from sticking out.

Moreover, the tip of the puncture needle 7 will not stick forward out through the through hole 11 of the skin contact part 10 also when the puncture needle cartridge 2 is picked up with fingers after disposal, and therefore a high level of safety is achieved.

In the present embodiment, as described above, the disk-shaped skin contact part 10 perpendicular to the puncture needle 7 exists in front of the puncture needle 7 even when the protective cap 13 is separated from the lancet body 6, and therefore safety is increased since the puncture needle 7 will not accidentally hurt hands or the like when the puncture needle cartridge 2 is removed from the puncture instrument 1 for disposal.

INDUSTRIAL APPLICABILITY

As stated above, in the present invention, the planar skin contact part perpendicular to the puncture needle exists in front of the puncture needle even when the protective cap is separated from the lancet body, and therefore safety is increased since the puncture needle will not accidentally hurt hands or the like when the puncture needle cartridge is removed from the puncture instrument for disposal.

Accordingly, the invention is expected to be utilized as a puncture needle cartridge for use in, for example, measuring blood sugar level and as a puncture instrument using the cartridge.

DESCRIPTION OF THE SYMBOLS

1: Puncture instrument
2: Puncture needle cartridge
3: Holder
4: Puncture needle holder
5: Puncture instrument mount
6: Lancet body
7: Puncture needle
8: Elastic object
9: Extension
10: Skin contact part
11: Through hole
12: Operation part
13: Protective cap
14: Separating part
15: First bent portion
16: Second bent portion
17: Cut
18: Guide protrusion
19: Hollow
20: Hollow
21: Protrusion
22: Biasing object
23: Operation button
24: Lock mechanism
25: Stopper
26: Ejecting operation lever
27: Hollow

The invention claimed is:

1. A puncture instrument comprising:
a puncture needle cartridge comprising:
    a columnar lancet body having a puncture needle on a front end side thereof and a puncture instrument mount on a rear end side thereof;
    a protective cap covering the puncture needle;
    a skin contact part positioned in front of a tip of the puncture needle, having a planar shape perpendicular to the puncture needle, and formed with a through hole to put the protective cap through;
    an elongate extension extending from the skin contact part toward a rear end of the puncture needle cartridge;
    an elastic object for coupling the elongate extension to the columnar lancet body and biasing the tip of the puncture needle toward the rear end side of the columnar lancet body behind the skin contact part;
a holder into which the puncture instrument mount is inserted;
a biasing object for accumulating biasing force against the columnar lancet body in a state in which the puncture needle cartridge is held by the holder; and
a puncture operation part for releasing the biasing force of the biasing object,
wherein a rear portion of the elongate extension is deformable toward the columnar lancet body,
wherein a space is defined between the columnar lancet body and a bent portion of the elastic object which bends convexly toward the columnar lancet body, and
wherein the columnar lancet body, the elastic object, the elongate extension, the skin contact part, and the protective cap are integrally formed of plastic.

2. The puncture instrument according to claim 1, wherein:
the bent portion of the elastic object is a first bent portion,
the elastic object comprises a second bent portion, and
a space is defined between the columnar lancet body and the second bent portion of the elastic object which bends convexly toward the elongate extension.

3. The puncture instrument according to claim 1, wherein the protective cap is coupled, via a breakable separating part, to a puncture needle holder of the columnar lancet body for holding the puncture needle, and has an operation part on a front end side thereof.

4. The puncture instrument according to claim 1, wherein the elongate extension is one of two elongate extensions, the two elongate extensions being opposed to each other across the through hole.

5. The puncture instrument according to claim 1, wherein the elongate extension is plate-shaped.

6. The puncture instrument according to claim 1, wherein the elastic object is folded elongate plate-shaped.

* * * * *